US00PP14402P29

(12) United States Plant Patent
Miranda

(10) Patent No.: US PP14,402 P2
(45) Date of Patent: Dec. 23, 2003

(54) CALADIUM PLANT NAMED 'FLORIDA WHITE RUFFLES'

(50) Latin Name: *Caladium×hortulanum*
Varietal Denomination: Florida White Ruffles

(75) Inventor: Baldwin D. Miranda, Naples, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 10/291,096

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Caladium plant named 'Florida White Ruffles', characterized by its compact and densely-foliated plant habit suitable for container production; upright, outwardly arching and symmetrical plant form; and white and dark green bi-colored leaves that are lanceolate in shape.

1 Drawing Sheet

Botanical classification/cultivar designation: *Caladium× hortulanum* cultivar Florida White Ruffles.

BACKGROUND OF THE INVENTION

The present Invention relates to a new and distinct cultivar of Caladium plant, botanically known as *Caladium× hortulanum*, commercially referred to as a lance-leaf Caladium, and hereinafter referred to by the cultivar name Florida White Ruffles.

The new cultivar is a product of a planned and controlled breeding program conducted by the Inventor in Bradenton, Fla. The objective of the breeding program is to create densely-foliated compact Caladium cultivars with uniquely variegated foliage.

The new cultivar originated from a cross-pollination made in 1985 of the *Caladium×hortulanum* cultivar Aaron, not patented, as the female, or seed, parent, with the *Caladium× hortulanum* cultivar Red Frill, not patented, as the male, or pollen, parent. The cultivar Florida White Ruffles was discovered and selected in 1986 as a plant within the progeny of the stated cross-pollination in a controlled environment in Bradenton, Fla.

Asexual propagation of the new cultivar by tuber divisions in Bradenton, Fla., has shown that the unique features of this new Caladium plant are stable and reproduced true to type in successive generations of asexual propagation.

SUMMARY OF THE INVENTION

The new Caladium has not been observed under all possible environmental conditions. The phenotype may vary somewhat with variations in environment such as temperature and light intensity, without, however, any variance in genotype.

The following traits have been repeatedly observed and are determined to be the unique characteristics of 'Florida White Ruffles'. These characteristics in combination distinguish 'Florida White Ruffles' as a new and distinct cultivar:

1. Compact and densely-foliated plant habit suitable for container production.

2. Upright, outwardly arching and symmetrical plant form.
3. White and dark green bi-colored leaves that are lanceolate in shape.

Plants of the new Caladium can be compared to plants of the female parent, the cultivar Aaron. When grown in side-side comparisons in Bradenton, Fla., plants of the new Caladium differed from plants of the cultivar Aaron, in the following characteristics:

1. Plants of the new Caladium were short than plants of the cultivar Aaron.
2. Plants of the new Caladium had more leaves per plant than plants of the cultivar Aaron.
3. Plants of the new Caladium had lanceolate-shaped leaves whereas plants of the cultivar Aaron had cordate-shaped leaves.

Plants of the new Caladium can be compared to plants of the male parent, the cultivar Red Frill. When grown in side-side comparisons in Bradenton, Fla., plants of the new Caladium differed primarily from plants of the cultivar Red Frill as plants of the cultivar Red Frill had red and dark green bi-colored leaves.

Plants of the new Caladium are similar in leaf coloration to the cultivars White Wing, not patented, and Jackie Suthers, not patented. However, when grown in side-side comparisons in Bradenton, Fla., plants of the new Caladium differed from plants of the cultivars White Wing and Jackie Suthers, in the following characteristics:

1. Plants of the new Caladium were shorter and more compact than plants of the cultivars White Wing and Jackie Suthers.
2. Plants of the new Caladium had narrower leaves, but more leaves per plant than plants of the cultivars White Wing and Jackie Suthers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Caladium. The photograph is a side perspective view of a typical plant of 'Florida White Ruffles' grown in a container.

DETAILED BOTANICAL DESCRIPTION

The aforementioned photograph, following observations, measurements and comparisons describe seven-week old plants (from planting a tuber division) grown in Bradenton, Fla. during the spring and summer in a shaded glass-covered greenhouse and under commercial production conditions in 15-cm containers. During the production of the plants, day temperatures were about 32° C., night temperatures were about 21° C. and light levels were about 2,000 to 3,000 foot-candles.

In the following description, color references are made to The Royal Horticultural Society Colour Chart except where general terms of ordinary dictionary significance are used.

Botanical classification: *Caladium×hortulanum* cultivar Florida White Ruffles.

Parentage:

*Female, or seed, parent.*—*Caladium×hortulanum* cultivar Aaron, not patented.

*Male, or pollen, parent.*—*Caladium×hortulanum* cultivar Red Frill, not patented.

Propagation:

*Type.*—By tuber divisions.

*Tuber description.*—Number of dominant buds per tuber: About 6 to 8. Diameter: About 6.4 to 8.9 cm. Color: Epidermis, 200B; interior, 20D.

*Time to initiate roots on a tuber division.*—About 9 days at 27° C.

*Time to produce a fully rooted tuber division.*—About 37 days at 27° C.

*Root description.*—Dense, thick and white in color.

Plant description:

*Plant habit.*—Compact and densely-foliated, suitable for 10 to 20-cm containers.

*Plant form.*—Upright, outwardly arching and symmetrical plant habit.

*Growth habit.*—Mostly erect when leaves are developing, becoming outwardly arching as leaves develop.

*Plant height.*—About 20 cm from soil level to top of leaf plane.

*Plant spread.*—About 35 cm.

*Foliage description.*—Quantity: About 36 per plant. Length: About 15 cm. Width: About 8 cm. Shape: Lanceolate. Apex: Acuminate. Base: Sagittate. Margin: Entire; slightly undulate. Aspect: Initially upright, then outwardly arching. Texture, upper and lower surfaces: Smooth, glabrous, durable and flexible. Venation pattern: Penniform. Color: Upper surface: Margins, 139A; irregular mottling parallel to the margin, 157B; center, close to 155C; venation, 156B; 1 mm wide line at the petiole attachment, 185A. Lower surface: Margins, 191A; center, close to 155C; venation, close to 155B. Petiole: Aspect: Mostly erect. Length: About 20 cm. Diameter: About 3 to 5 mm. Strength: Strong. Color: Covered with brown, 200D, speckles.

*Flower description.*—Flower development has not been observed on plants of the new Caladium.

Disease/pest resistance: Plants of the new Caladium have not been observed to be resistant to pathogens or pests common to Caladium.

Temperature/weather tolerance: Plants of the new Caladium have been observed to be tolerant to temperatures as low as 10° C. and as high as 38° C. Plants of the new Caladium have been observed to be tolerant to rain and wind. Plants of the new Caladium will tolerate full sun conditions in Florida without leaf scorching.

It is claimed:

1. A new and distinct cultivar of Caladium plant named 'Florida White Ruffles', as illustrated and described.

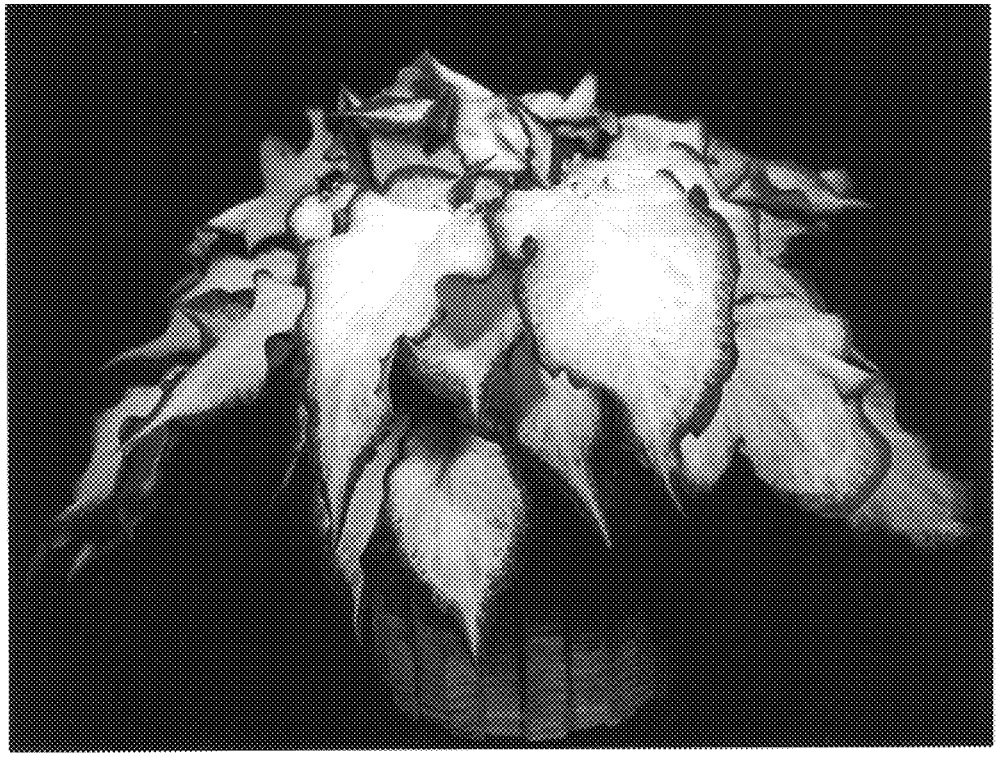

* * * * *